United States Patent [19]

Gevas et al.

[11] Patent Number: 5,023,077

[45] Date of Patent: Jun. 11, 1991

[54] IMMUNOGENIC COMPOSITIONS AND METHODS FOR THE TREATMENT AND PREVENTION OF GASTRIC AND DUODENAL ULCER DISEASE

[75] Inventors: Philip C. Gevas, Honolulu, Hi.; Stephen L. Karr, Jr., Davis; Stephen Grimes, both of Davis, Calif.; Richard L. Littenberg, Kai Lua, Hi.

[73] Assignee: Aphton Corporation, Woodland, Calif.

[21] Appl. No.: 301,353

[22] Filed: Jan. 24, 1989

[51] Int. Cl.$^5$ ............................ C07K 7/06; C07K 7/30; A61K 39/00; A61K 37/24

[52] U.S. Cl. ...................................... 424/88; 530/328; 530/329; 530/330; 514/16; 514/17; 514/18

[58] Field of Search ...................... 514/13, 14, 15, 16, 514/17, 18; 424/88; 530/326, 327, 328, 329, 330

[56] References Cited

U.S. PATENT DOCUMENTS

| | | | |
|---|---|---|---|
| 3,931,141 | 1/1976 | Wissmann et al. | 530/329 |
| 4,565,805 | 1/1986 | Smirnov et al. | 514/17 |
| 4,687,759 | 8/1987 | Martinez et al. | 514/18 |

OTHER PUBLICATIONS

Kothary, P. et al., *Biochem. Biophys. Res. Commun.*, 146(2): 884–888, 1987.
Nemeth, J. et al., *Chem. Abs.*, 98:51653w, p. 495, 1982.
Dochray, G., *Chem. Abs.*, 94:119200w, p. 506, 1980.
Yamaguchi, K. et al., *Chem. Abs.*, 100:154661m, p. 373, 1983.
Dockray, "Regulatory Peptides", 1, 169–186 (1980).
Yanaihara et al., "Biomedical Research", 1, 242–247 (1980).
Yanaihara et al., "Gut Peptides", 26–33 (1979).
Sugano et al., *The Journal of Biological Chemistry*, vol. 260, No. 21, Sep. 25, 1985, pp. 11724–11729.
Jaffe et al., *Gastroenterology*, vol. 58, No. 2, Feb. 1970, pp. 151–156.
Jaffee et al., *Surgery*, vol. 69, No. 2, Feb. 1971, pp. 232–237.
Jaffe et al., *Surgery*, vol. 65, No. 4, Apr., 1969, pp. 633–639.
Hughes et al., *Digestive Diseases*, vol. 21, No. 3, Mar. 1976, pp. 201–204.
Wunsch et al., *Z. Physiol. Chem.*, Jun. 1982, pp. 666–669.
Larsson, Neurohistochemoistry: Modern Methods and Applications, 1986, pp. 527–567.
Moroder et al., Gastrin and Cholecystokinin, Chemistry, Physiology and Pharmacology, 1987, pp. 21–32.
Dockray et al., *Gastroenterology*, vol. 68, No. 2, Feb. 1975, pp. 222–230.
Azuma et al., *Gastroenterologia Japonica*, vol. 21, No. 4, Aug. 1986, pp. 319–324.
Iwanaga et al., *Biomedical Research*, 1, 1980, pp. 316–320.
Varndell et al., *Experientia*, 39, 1983, pp. 713–717.
Larsson et al., *The Journal of Histochemistry and Cytochemistry*, vol. 25, No. 12, 1977, pp. 1317–1321.
Rehfeld et al., *Scand. J. Clin. Lab. Invest.*, 30, 1972, pp. 221–232.
De Magistris et al., *Analytical Biochemistry*, 102, 1980, pp. 126–133.
Rehfeld et al., *Regulatory Peptides*, 2, 1981, pp. 333–342.

*Primary Examiner*—Howard E. Schain
*Assistant Examiner*—Susan Perkins
*Attorney, Agent, or Firm*—White & Case

[57] ABSTRACT

Immunogenic compositions useful for the treatment or prevention of gastric or duodenal ulcer disease are disclosed. The immunogenic compositions effectively operate by inducing antibodies in a subject which selectively neutralize specific peptide gastric hormones and inhibit the binding of the hormones to physiological receptors thus limiting the secretion of stomach acid. Pharmaceutical compositions comprising effective amounts of the immunogenic compositions and methods of treatment using the compositions are also disclosed.

8 Claims, 8 Drawing Sheets

IMMUNOGENIC COMPOSITIONS AND METHODS FOR THE TREATMENT AND PREVENTION OF GASTRIC AND DUODENAL ULCER DISEASE

BACKGROUND AND DESCRIPTION OF THE INVENTION

Peptic ulcer disease exists in two forms, duodenal ulcers and gastric ulcers. Central to the cause of duodenal ulcers, is the production of excess stomach acid and pepsin and a rapid gastric emptying time. This results in an increase in duodenal exposure to secreted acid and enzymes, and in mucosal damage.

The second form of the disorder, gastric ulcer disease, is caused by increased stomach acid and a breakdown of the complex stomach defenses that normally protect the gastric mucosa from acid damage. Although the two conditions have different etiologies, both benefit from a reduction in gastric acid secretion.

Because excess stomach acid is a central cause of ulcers, antacid preparations are commonly used as one method of treatment. This method merely neutralizes stomach acid after it is produced. Consequently, large quantities of antacids must be consumed on an ongoing basis to neutralize acid which is continually produced in the stomach. Antacids do not cure the disease because they do not affect the source of acid production.

Gastric acid is produced in a specialized stomach cell, the parietal cell. Parietal cells can be stimulated to secrete acid by acetylcholine, histamine and gastrin, upon the binding of each of these compounds with specific receptors on the surface of the cell. Of these the most potent stimulator of acid secretion is the peptide hormone gastrin.

Current approaches to the control and cure of peptic ulcers center upon devising drugs that inhibit the ability of one or more of these compounds to stimulate acid production or secretion. The most effective group of drugs approved for sale are the H2 antagonists (e.g. Tagamet ® and Zantac ®) which block the histamine H2 receptors on gastric parietal cells and inhibit acid secretion. These drugs, however, require relatively large doses on a daily basis and may induce several undesirable side effects. In cases where H2 antagonists have cured ulcers, relapses occur in almost 100% of cured individuals within a year of discontinuation of treatment. Other drugs have also exhibited problems, including low efficacy and unacceptable levels of toxicity. In the case the peptide hormone gastrin, no usable chemical antagonists have been identified.

Gastrin has several important functions in the gastrointestinal tract, the two most important being stimulation of acid secretion and stimulation of the growth of cells in the gastrointestinal tract. The hormone exists in at least two molecular forms, heptadecagastrin ("G17") and tetratriacontagastrin ("G34") named according to the number of amino acid ("AA's") residues in each molecule G34 and G17 are identical in structure at the carboxy terminus, which is the binding site of the hormones with receptors G17 constitutes the 17 carboxy terminal ( C-terminal") end residues of G34. G34 consists of the 17 C-Terminal end residues which comprise G17 and an additional different amino acid sequence of 17 amino terminal ("N-terminal") residues. When G34 is split by trypsin a G17 subunit and a non-hormonal 17 amino acid subunit results. Though G17 can be obtained by trypsin cleavage of G34, it is currently believed that this is not the normal route for the in vivo generation of G17. It appears that, in vivo, each form is generated separately from its own prohormone.

Although G17 and G34 are thought to be equipotent on a molar basis as stimulators of acid release, G34 is most probably responsible for the stimulation of growth of the gastrointestinal mucosa and the maintenance of the basal acidity of the stomach. G34 is the principal form present during interdigestive periods. G34 has a serum half life approximately six times as long as G17 (40 minutes versus 6 minutes) and is produced in both the stomach and the duodenum. Alternatively, G17 is the primary stimulator of meal induced gastric acid secretion. G17 is 1500 times more potent than histamine and makes up 90% of the antral (stomach) gastrin. G17 accounts for roughly 60% of the gastrin-mediated acid release.

The prior art in the area of gastrin immunology mainly concerns the induction of antibodies useful for identifying anatomic sites containing or producing gastrin G17 or G34 in laboratory animals; see Sugano, K., et al., 1985, "Identification and characterization of glycine-extended post translational processing intermediates of progastrin in porcine stomach", *J. of Biological Chemistry* 250: 11724-11729; Vaillant, C., et al., 1979, Cellular origins of different forms of gastrin: The specific immunocytochemical localization of related peptides. *J. Histochem Cytochem* 27:932-935; Larsson, L. I. et al., 1977, "Characterization of antral gastrin cells with region-specific antisera". *J. Histochem. Cytochem* 25: 1317-1321. The antisera reported in these publications contained antibodies of numerous specificities, for a variety of antigenic epitopes on gastrin molecules.

Attempts to control gastrin levels by anti-gastrin antibodies induced by active immunization or passive administration of preformed antibodies such as those reported in Jaffe, B. M., et al., 1971, "Gastrin resistance following immunizations to the C-terminal tetrapeptide amide of gastrin, *Surgery* 69: 232-238; Jaffe, B. M., et al., 1970, "Inhibition of endogenous gastrin activity by antibodies to the carboxyl terminal tetrapeptide amide of gastrin", *Gastroenterology* 58: 151-156; Jaffe et al., 1969, "Inhibition of endogenous gastrin activity by incubation with antibodies to the C-terminal tetrapeptide of gastrin. *Surgery* 65: 5633-639 are different from the present invention in that the immunogen used was derived from the carboxyl terminal tetrapeptide amino acid sequence common to G17, G34, and to another important hormone, cholecystokinin ("CCK"). The immunogen of Jaffe et al. is thus of no practical value as an anti-gastrin vaccine component; on the contrary, it would produce a deleterious state in which all gastrin activity and other hormone function of G17, G34, together with CCK, would be blocked and eliminated by immunization.

This invention provides a novel immunological approach to the control and regulation of peptic ulcers. According to the invention, antibodies are induced in the patient by passive or active immunization with immunogens that selectively target specific forms of gastrin.

Since the different forms of gastrin vary in function, it is necessary to selectively neutralize specific forms of gastrin to control specific functions. To regulate gastrin mediated secretion of stomach acid following meals (the principal source of excess stomach acid relating to ulcers), an immunogen must specifically target G17.

In order to selectively neutralize G17, one or more antigenic epitopes on G17 that are not found on G34 or cholecystokinin which exhibits carboxy terminal homology with gastrin must be identified. As discussed above even though the C-terminus of G17 and G34 are identical the N-terminus of G17 is very different from that of G34. This results in antigenic epitopes that are unique to G17 and can be separately targeted. We have identified and mapped such a unique epitope on G17. The present invention concerns immunogens comprising this unique epitope. These immunogens result in high levels of anti-G17 antibodies that do not crossreact with G34 and block some or all of G17 stimulation of gastric acid secretion while still allowing G34 and CCK, which share with G17 a common receptor, to carry out their physiologic function. The regulation of acid secretions can also involve the neutralization of G34; we have also identified and mapped unique epitopes on G34 that are not found on G17 or CCK.

Our immunoneutralizing approach has several attractive advantages over current treatments for peptic ulcer. One of these advantages is the overcoming of the major problem of patient compliance since a daily dose of a drug is not required. This invention treats ulcers b preventing the release of excess stomach acid, unlike antacids that neutralize secreted acid. By administering our synthetic peptide as an immunogen, the frequency and quantity of treatment administration is decreased, while at the same time long-lasting control of acid production, reduced side effects and easier patient administration are provided. Unlike conventional anti-ulcer drugs, antibodies generated by the peptide immunogens are very specific to their target. They do not cross the blood-brain barrier, and their use avoids certain complications encountered with drugs. In addition, unlike this invention, agonists or antagonists of G17 cannot be used to specifically control ulcers because such compounds would also occupy the receptors for G34 and CCK, which have identical receptor binding sites with G17.

The immunogens against one form of gastrin, "little gastrin", or G17, are constructed to produce an anti-gastrin vaccine component that will induce a selective and specific antibody response to G17 in the vaccinated human or other vertebrate, but not to G34 or CCK. This selective immunization to produce G17 specific antibodies is crucial to avoid producing antibodies specific for or cross reactive with G34, which might during the treatment of a specific condition induce undesirable side effects by blocking G34 physiologic functions. The antibodies resulting from the immunization with such immunogens target the chemical structure of G17 which is antigenically and immunogenically unique from the structure of G34. The amino acid residues beginning from the amino terminus (amino acid residue number one) of G17 and extending up to and including amino acid residue number 12 having the sequence pyro-Glu-Gly-Pro-Trp-Leu-Glu-Glu-Glu-Glu-Glu-Ala-Tyr, are used to prepare the immunogens of the invention. For simplicity this sequence can be written based upon the international code for amino acids as pyro-E-G-P-W-L-E-E-E-E-E-A-Y. The immunogens may contain a part or all of this sequence. For example, immunogens may be prepared by using the following specific peptide sequences: pGlu-Gly-Pro-Trp-Leu-Glu-Glu-Glu-, pGlu-Gly-Pro-Trp-Leu-Glu-Glu-, pGlu-Gly-Pro-Trp-Leu-Glu-, pGlu-Gly-Pro-Trp-Leu- and pGlu-Gly-Pro-Trp-. The last 5 carboxyterminal end amino acids of the G17 chemical structure (residues 13–17) are preferably not used, because this sequence is a common antigenic sequence between G17, G34, and at least one other hormone, cholecystokinin (CCK). Fragments, extensions, or other subsets of the natural hormone and of this 12 amino acid sequence of G17 may be used. One or more other amino acids may also be substituted for those of the natural sequence, so that increased or decreased binding capacity, specificity and/or titer of the antibody response against G17 may be induced in the vaccinated host by the immunogen.

The immunogens of the invention may be produced through synthetic or other processes commonly used in the art including standard peptide synthesis technologies; methods employing recombinant DNA and associated technologies; antigen mimicking methods including antibody-internal image technology and any other related methodologies that produce a structure that immunologically resembles the antigenic structures of G17 (mimotopes) and others.

In other embodiments of the invention the use of preformed G17 specific polyclonal and/or monoclonal antibodies and their derivatives or fragments produced by immunization, hybridoma, recombinant DNA or other technologies as a method of passive immunization for the control of gastric acid secretion stimulated by G17 may be used.

The present invention also provides immunogens against a second form of gastrin, "big gastrin" or G34. These immunogens are used to produce an anti-gastrin vaccine component that may be useful for the treatment or prevention of other gastrointestinal diseases and that will induce a selective and specific antibody response to G34 (but not to G17 or CCK) in the vaccinated human or other vertebrate. This selective immunization to produce G34 specific antibodies is crucial to avoid producing antibodies specific for or cross reactive with G17.

The G34 immunogens specifically target chemical structures of G34 which are antigenically and immunogenically unique from the structure of G17. The chemical structures of G34 utilized in this invention include, but are not limited to, the amino acid residues beginning from the amino terminus (amino acid residue number one) of G34 and extending up to and including amino acid residue number 22. The sequence of this peptide is pyro-Glu-Leu-Gly-Pro-Gln-Gly-Pro-Pro-His-Leu-Val-Ala-Asp-Pro-Ser-Lys-Lys-Gln-Pro-Trp-Lev. Based upon the international code for amino acids, this sequence is pyro-E-L-G-P-Q-G-P-P-H-L-V-A-D-P-S-K-K-Q-G-P-W-L-. The G34 immunogens may contain part or all of this sequence. The sequence of the last 12 amino acids of the G34 chemical structure (residues 23–34) are preferably not used in this invention because this sequence is a common antigenic sequence between G17 and G34. The sequence of amino acids are also not used since the sequence 29–34 has common antigenic sites with cholecystokinin. It is contemplated that the use of any fragments, extensions, or other subsets of the natural hormone and of this 22 amino acid sequence may be used as immunogens. One or more other amino acids may also be substituted for those of the usual natural sequence, so that increased or decreased binding capacity, specificity and/or titer of the antibody response against G34 may be induced in the vaccinated host by the immunogen.

The G34 immunogen may be produced by any process commonly used in the art including, for example, standard peptide synthesis technologies; methods employing recombinant DNA and associated technologies; antigen mimicking methods including antibody-internal image technology and any other related methodologies that produce a structure that immunologically resembles the antigenic structures of G34 (mimotopes).

Preformed G34 specific monoclonal antibodies and their derivatives or fragments produced by hybridoma, recombinant DNA or other technologies may also be used as a method of passive immunization for the control o gastric acid secretion stimulated by G34.

It may be desirable in some applications to immunize against both G17 and G34. In this embodiment G17 and G34 immunogens are used in combination including optionally an immunogen with an epitope common to G17 and G34, so that antibodies against both G17 and G34 are induced by the immunized host. The immunogens of this invention are therefore useful for more than just the treatment or prevention of ulcers. The immunogens may be used to treat any disease in which the gastrin stimulated secretion of stomach acid is a factor.

For the G17 and/or the G34 epitopes of this invention to induce antibodies, it may be necessary to increase their immunogenicity by chemically coupling them to other molecules. Such molecules are termed "carriers". Any molecule capable of serving as a carrier may be used. Examples of carriers for this purpose include: diphtheria toxoid, tetanus toxoid, keyhole limpet hemocyanin, bovine serum albumin, etc. Fragments of these carriers, including single epitopes, may also be used. Any method of chemically coupling the epitopes to the carriers may be followed. A preferred method utilizes the bifunctional linking agent EMCS described in U.S. Pat. No. 4,302,386; Lee et al., 1981.

The epitopes can be alternatively rendered immunogenic by crosslinking a number of epitopes. For this purpose, it may be necessary to extend the molecule bearing the G17 or G34 epitope by the addition of selected compounds that provide structures through which the crosslinking will occur. These additions must not disrupt the structure of the gastrin epitope, because the capacity to induce anti-gastrin antibodies would be lost. For example, to the carboxy terminal end of the G17 epitope pyro-E-G-P-W-M-E-E is added the amino acid sequence K-R-P-P-P-P-K, to give pyro-E-G-P-W-M-E-E-K-R-P-P-P-P-K. This molecule is then polymerized with glutaraldehyde, which crosslinks the lysine K residues, to form the crosslinked immunogen. This crosslinked immunogen should induce specific antibodies against G17.

In addition, the carrier and crosslinking methods may be used in combination. Thus, carrier epitopes that enhance immunogenicity and epitopes unique to G17 and/or G34 are integrated into the same polymer. For example, one or more carrier epitopes from Diphtheria toxoid may be crosslinked in combination with the G17 epitope pyro-E-G-P-W-L-E-E-K-R-P-P-P-P-K by the glutaraldehyde approach to yield an immunogenic copolymer. In a second example, a carrier epitope can be built into the molecule that contains the G17 epitope, then this larger molecule is crosslinked with glutaraldehyde. As a third example, the G17 epitope bearing molecule pyro-E-G-P-W-L-E-E-K-R-P-P-P-P-K may be crosslinked with a crosslinking agent that itself contains a carrier epitope.

The means by which anti-gastrin antibodies prevent acid release has not been thoroughly established. Without being bound by theory, we believe that the acid suppressive effect of our immunogen is due to the binding of anti-gastrin antibodies to gastrin (G17 and/or G34) in the blood, and thereby preventing the binding of gastrin to its physiological receptors on the surfaces of parietal cells. Thus, gastrin is prevented from signaling parietal cells to secrete acid into the stomach.

Administration of these immunogens, compositions containing them, or pharmaceutically acceptable and immunologically effective derivatives thereof, may be via any of the conventionally accepted modes of administration of agents which exhibit immunogenicity. These include oral or parenteral administration.

The compositions used in these vaccines may be in a variety of forms. These include, for example, solid, semisolid and liquid dosage forms, such as powders, liquid solutions or suspensions, suppositories, injectable and infusible solutions. The preferred form depends on the intended mode of administration and therapeutic applications.

The compositions also will preferably include conventional pharmaceutically acceptable vehicles or carriers and may include other medicinal agents, carriers, adjuvants, excipients, etc., e.g., human serum albumin or plasma preparations. Preferably, the compositions of the invention are in the form of a unit dose. The amount of active compound administered as a vaccination or as a medicament at one time, or over a period of time, will depend on the subject being treated, the manner and form of administration, and the judgment of the treating physician. However, an effective dose may be in the range of from about 1 ug to about 10 mg of the immunogen of this invention, preferably about 100 (micrograms "ug") to about 2 mg; it being recognized that lower and higher doses may also be useful.

The examples illustrate specific embodiments of the invention. It should be understood that these examples are for illustrative purposes only, and are not to be construed as limiting this invention in any manner.

EXAMPLE 1

Figure 1:
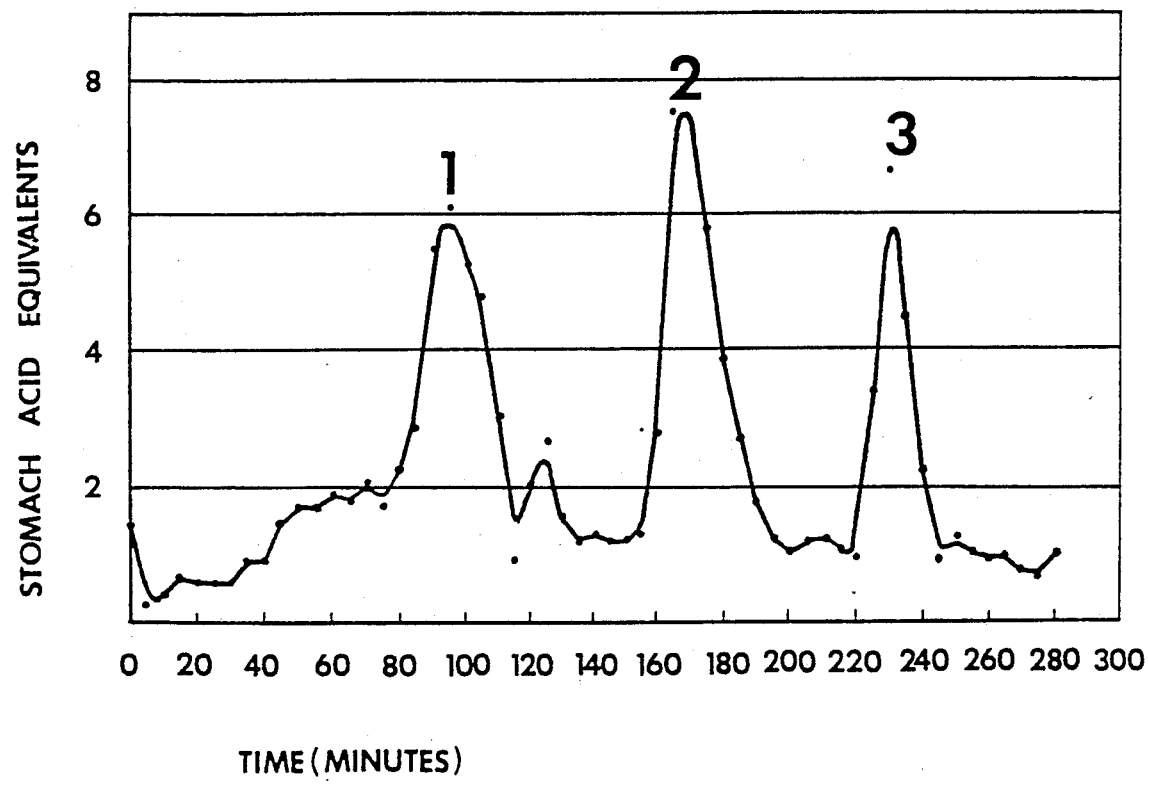
FIG. 1: illustrates the stomach acid secretions over time of a control rat injected sequentially with hG17, antisera raised against an unrelated peptide and hG17.

Immunogens capable of inducing specific immune responses to either G17 or to G34 were prepared by standard solid state synthesis methods. Each peptide was characterized as to amino acid content and purity.

Peptides with the following amino acid sequences were synthesized:

Peptide 1- Human G17(1-6) ("hG17(6)"): pGlu-Gly-Pro-Trp-Leu-Glu-Arg-Pro-Pro-Pro-Cys Peptide 2- Human G17(1-5) ("hG17(5)"): pGlu-Gly-Pro-Trp-Leu-Arg-Pro-Pro-Pro-Cys Peptide 3- Human G17(1-4) ("hG17(4)"): pGlu-Gly-Pro-Trp-Arg-Pro-Pro-Pro-Cys Peptide 4- Rat G17(1-6) ("rG17(6)"): pGlu-Arg-Pro-Pro-Leu-Glu-Arg-Pro-Pro-Pro-Cys Peptide 5- Human G34(1-6) ("hG34(6)"): pGlu-Leu-Gly-Pro-Gln-Gly-Arg-Pro-Pro-Pro-Cys Peptide 6- Human G34(13-22) ("hG34/G17 combination"): Asp-Pro-Ser-Lys-Lys-Gln-Gly-Pro-Trp-Leu-Pro-Pro-Pro-Cys Each of these peptides were conjugated to amino groups present on a carrier such as Diphtheria toxoid ("DT") via the terminal peptide cysteine residue utilizing heterobifunctional linking agents containing a succinimidyl ester at one end and maleimide at the other end of the linking agent.

To accomplish the linkage between any of Peptides 1-6 above and the carrier, the dry peptide was dissolved in 0.1 M Sodium Phosphate Buffer, pH 8.0, with a thirty molar excess of dithiothreitol ("DTT"). The solution was stirred under a water saturated nitrogen gas atmosphere for four hours. The peptide containing reduced cysteine was separated from the other components by chromatography over a G10 Sephadex column equilibrated with 0.2 M Acetic acid. The peptide was lyophilized and stored under vacuum until used. The carrier was activated by treatment with the heterobifunctional linking agent e.g Epsilon-maleimidocaproic acid N-hydroxysuccinimide ester, ("EMCS"), in proportions sufficient to achieve activation of approximately 25 free amino groups per $10^5$ molecular weight of carrier. In the specific instance of diphtheria toxoid, this amounted to the addition of 6.18 mg of EMCS (purity 75%) to each 20 mg of diphtheria toxoid.

Activation of diphtheria toxoid was accomplished by dissolving each 20 mg aliquot of diphtheria toxoid in 1 ml of 0.2 M Sodium Phosphate Buffer, pH 6.45. Aliquots of 6.18 mg EMCS were dissolved into 0.2 ml of Dimethyl Formamide ("DMF"). Under darkened conditions, the EMCS was added dropwise in 50 microliter ("ul") amounts to the DT with stirring. After 2 hours of incubation in darkness, the mixture was chromatographed on a G50 Sephadex column equilibrated with 0.1 M Sodium Citrate buffer, pH 6.0, containing 0.1 mM EDTA.

Fractions containing the EMCS activated diphtheria toxoid were concentrated over a PM 10 ultrafiltration membrane under conditions of darkness. The protein content of the concentrate was determined by either the Lowry or Bradford methods. The EMCS content of the carrier was determined by incubation of the activated carrier with cysteine-HCl followed by reaction with 10 mM of Elman's Reagent 5,5'dithio-bis (2-nitrobenzoic acid) 10mM. The optical density difference between a blank tube containing cysteine-HCl and the sample tube containing cysteine-HCl and carrier was translated into EMCS group content by using the molar extinction coefficient of $13.6 \times 10^3$ for 5-thio-2-nitro benzoic acid at 412 nm.

The reduced cysteine content (—SH) of the peptide was also determined utilizing Elman's Reagent. Approximately 1 mg of peptide was dissolved in 1 ml of nitrogen gas saturated water and a 0.1 ml aliquot of this solution was reacted with Ehman's Reagent. Utilizing the molar extinction coefficient of 5-thio-2-nitro-benzoic acid ($13.6 \times 10^3$), the free cysteine —SH was calculated. An amount of peptide containing sufficient free —SH to react with each of the 25 EMCS activated amino groups on the carrier was dissolved in 0.1 M Sodium Citrate Buffer, pH 6.0, containing 0.1 mM EDTA, and added dropwise to the EMCS activated carrier under darkened conditions. After all the peptide solution had been added to the carrier, the mixture was incubated overnight in the dark under a water saturated nitrogen gas atmosphere.

The conjugate of the peptide linked to the carrier via EMCS is separated from other components of the mixture by chromatography over a G50 Sephadex column equilibrated with 0.2 M Ammonium Bicarbonate. The conjugate eluted in the column void volume is lyophilized and stored desiccated at 20° C. until used.

The conjugate may be characterized as to peptide content by a number of methods known to those skilled in the art including weight gain, amino acid analysis, etc. Conjugates of Peptides 1-6 and diphtheria toxoid produced by these methods were determined to have 20-25 moles of peptide per $10^5$ MW of carrier and all were considered suitable as immunogens for immunization of test animals.

EXAMPLE 2

As examples of the utilization of peptides containing sequences of human gastrin as immunogens to induce immune responses against hG17 or hG34, we have immunized rats with the conjugate immunogens constructed from Peptides 1-6 of Example 1 and Diphtheria toxoid ("DT") (referred to as Immunogens 1-6, respectively).

Six different groups of 15 Sprague-Dawley female rats (200 gm. body weight) were each immunized with one of the immunogens. Each animal was injected subcutaneously with 0.25 ml of immunogen consisting of 0.1 mg of conjugate dissolved in 0.125 ml of 0.1 M Sodium Phosphate Buffered Saline, pH 7.3, emulsified with an equal volume of Squalene-Arlacel (4:1 ratio volume/volume) vehicle containing 0.05 mg of Nor MDP as adjuvant.

Two additional groups of 15 rats were immunized with a peptide-DT conjugate in which the peptide had no sequence homology with gastrins so as to act as a negative immunization control.

Each rat was given an injection of immunogen at 0, 3, and 6 weeks. Blood was collected from each rat at 3, 6, and 8 weeks of the experiment. Serum was collected from each blood sample and stored at −20° C. until utilized in assays to determine the presence of anti-gastrin antibodies.

Two types of assays were used to detect antigastrin antibodies. A solid-phase enzyme linked immunosorbent assay (ELISA) and a liquid phase radioimmunoassay (RIA) were employed.

ELISA was used to screen for reaction or cross reaction of antisera raised against Peptides 1-6 with Peptides 1-6 or with hG17, hG34, or hCCK. The RIA was used to quantitate the antibody levels in the antiserum of each immunized animal that was reacted with hG17 or hG34 by determining the antigen binding capacity (ABC), expressed as pg hormone bound per microliter ("ul") of antiserum (pg/ul).

The ELISA was conducted by coating polystyrene 96 well plates (Immulon II ™) with 1 ug/ml of Peptides 1-6, hG17, hG34, or hCCK antigen. Serial dilutions of test antisera of $1 \times 10^{-1}$ to $1 \times 10^{-8}$ were incubated with each test peptide for 30 minutes at room temperature. In some instances antisera raised against a particular peptide of the Peptides 1-6 were preincubated with large excesses of the other peptides of the Peptide 1-6 group or with hG17 or hG34 in an attempt to inhibit binding of the antiserum to its particular peptide and also to demonstrate the occurrence of antibodies in the antisera that were specific for the sequence (spacer) of each peptide that was common to all of Peptides 1-6 (e.g. Arg-Pro-Pro-Pro-Pro-Cys). After washing each well thoroughly to remove unbound antibody, each well was treated with biotinylated anti-rat immunoglobulin reagent for 30 minutes at room temperature. After another wash sequence to remove unbound anti-rat reagent, avidin-alkaline phosphatase conjugate was added and the mixture was incubated for an additional 30 minutes. The mixture was washed thoroughly to remove unbound avidin-alkaline phosphatase reagent, and the chromogenic substrate PNPP was added for a 10 minute period. The absorbance of each well was read at 490 mn after the 10 minute incubation.

The standard RIA procedure was followed. In the RIA, 0.1, 1.0 or 10.0 ul aliquots of antiserum were incubated with approximately 200 pg of $^{125}I$ labeled hG17 or 400 pg of labeled hG34. The antisera were incubated with label for 2 hours, and were followed by a precipitation of hormone-antibody complexes with 25% polyethylene glycol. Antigen binding capacities for each antiserum where then determined from the amount of radioactive hormone precipitated. To demonstrate the specificity of the reaction of the $^{125}I$ labeled hormone with the antisera, aliquots of the antisera were preincubated in some tests with excess amounts of the hormone that were not labeled with $^{125}I$ to inhibit binding o the antisera to the labeled hormone.

The specificities of the antibody responses induced by Immunogens 1-6 as measured by ELISA are depicted in Table 1. Immunogen 1, containing the peptide sequence of hG17 (1-6), induced antibodies that reacted strongly with hG17 and hG17 (1-6) peptide, but only weakly with hG34 (1-6) or hG34 (13-22). Antisera raised to Immunogen 1 did not react with hG34. Inhibition experiments with Peptides 1-6 suggest that the weak reactivity of anti-Immunogen 1 antibodies with hG34

(1-6) and G34 (13-22) peptides was due to the presence of antibodies that were induced by the spacer sequence (-Arg-Pro-Pro-Pro-Cys) common to all the peptide sequences of Immunogens 1-6.

Immunogens 2 and 3 induced antibody responses specific for hG17 that were much weaker than those induced by Immunogen 1 (Table 1). Inhibition experiments, suggested that the weak reactivities of anti-Imunogen 2 and 3 antibodies for Peptides 1-6 are specific for the common spacer sequence of Peptides 1-6.

Immunogen 4, containing the rat G17 sequence, induced antibodies that weakly reacted with Peptides 1-6, but not hG17 or hG34 (Table 1). Inhibition experiments suggested that these antibodies were directed against the spacer sequence common to Peptide 1-6.

Immunogen 5 hG34 (1-6), induced antibodies that strongly reacted with hG34 and Peptide 5, hG34 (1-6), but weakly with the other peptides and not at all with G17. Inhibition experiments suggested that the reactivity with Peptides 1-4 and 6 was due to anti-spacer specific antibodies.

TABLE 1

| | Reaction in ELISA with: | | | | | | |
|---|---|---|---|---|---|---|---|
| Antisera to: | hG17 | Peptide 1 hG17(1-6) | Peptide 2 hG17(1-5) | Peptide 3 hG17(1-4) | Peptide 4 rG17(1-6) | Peptide 5 hG34(1-6) | Peptide 6 hG34(13-22) | hG34 |
| Immunogen 1 hG17(1-6)-DT | ++ | +++ | + | ± | ± | ± | ± | O |
| Immunogen 2 hG17(1-5)-DT | + | ± | + | ± | ± | ± | ± | O |
| Immunogen 3 hG17(1-4)-DT | ± | ± | ± | ± | ± | ± | ± | O |
| Immunogen 4 rG17(1-6)-DT | O | ± | ± | ± | ± | ± | ± | O |
| Immunogen 5 hG34(1-6)-DT | O | ± | ± | ± | ± | ++ | ± | +++ |
| Immunogen 6 hG34(13-22)-DT | ± | ± | ± | ± | ± | ± | ± | ± |

+++ to +: Strongly reactive
±: Weakly reactive
O: No reaction

Immunogen 6, hG34 (13-22), induced antibodies that reacted weakly with Peptides 1-6, but not with hG17. Inhibition experiments demonstrated that the antibodies binding Peptides 1-6 were specific for the common spacer sequence.

All antisera were also tested against hCCk; none of the antisera bound to hCCk.

Table 2 demonstrates the RIA-measured antigen binding capacities ("ABC"8) versus hG17 or hG34 of antisera raised against Immunogens 1-6 after three immunizations of rats with 0.1 mg of conjugate.

TABLE 2

| Rats Immunized With: | Mean RIA ABC (pg/ul) | |
|---|---|---|
| | hG17 | hG34 |
| Immunogen 1 hG17(1-6)-DT | 19.29 | 0.00 |
| Immunogen 2 hG17(1-5)-DT | 7.59 | 0.00 |
| Immunogen 3 hG17(1-4)-DT | 2.15 | 0.00 |
| Immunogen 4 rG17(1-6)-DT | 0.00 | 0.00 |
| Immunogen 5 hG34(1-6)-DT | 0.00 | 6.38 |
| Immunogen 6 hG34(13-22) | 0.00 | 1.28 |

The liquid phase RIA demonstrated that Immunogens 1-3 containing the hG17 peptide sequence induced antibodies that reacted only with hG17 and that Immunogen containing the hG34 sequence, induced antibodies that reacted only with G34. Immunogen 6 induced very low ABC's to G34.

The ELISA and RIA assays thus demonstrate the specificity of the responses to hG17 or hG34 that are induced by Immunogens 1-6.

EXAMPLE 3

This example demonstrates the ability of antisera raised against Peptide 1 (hG17 (1-6)) to neutralize the in vivo acid stimulating activity of hG17. In this demonstration an amount of hG17 is mixed with an excess amount of anti-Peptide 1 antiserum sufficient to bind to all the hG17 prior to injection of the complex into a normal (non-immunized) rat.

In control experiments the amount of hG17 sufficient to stimulate an increase of acid secretion of at least 100% above nonstimulated acid secretion in normal rats was determined to be 0.4 ug of hG17 hormone per kg body weight.

Antisera from the rats immunized with Immunogen 1 were pooled and standard amounts of antisera were incubated with 200 pg $^{125}$I labeled hG17 after incubation with increasing amounts of cold hG17 as inhibitor. Based on this inhibition study 1 ml of antiserum was capable of binding 1000X the 0.4 ug/kg dose of hG17 to be administered to rats. As a safety factor, the 0.4 ug/kg (approximately 120 ng) of hormone was mixed with 2.5 ml of anti-hG17 specific antiserum raised against Immunogen 1.

Rats to be injected with hG17 complexed with anti-hG17 antibodies were surgically prepared for collection of stomach secretions by the perfused rat stomach procedure.

Under general anesthesia and following tracheostomy, the rat was cannulated via the esophagus and duodenum to allow continuous perfusion of the stomach with 0.9% saline. The stomach perfusate was collected as 5 minute interval samples and was titrated for acid content by neutralization with base (sodium hydroxide). Incremental and total acid input during the duration of the experiment an after each treatment was determined.

Each control or experimental test rat was first injected with 0.4 ug/kg hG17 to determine the rats total acid secretory response to this treatment. The first treatment was followed one hour later in test rats with an injection of 0.4 ug/kg of hG17 that had been premixed for one hour with 2.5 ml of anti-hG17 specific antiserum. Control rats received an injection of hG17 mixed with 2.5 ml of antiserum raised against an unrelated peptide. After one hour, a second injection of free hG17 was administered to the test and control rats; and stomach perfusate was collected for an additional hour. The total acid output induced by the second and third injections of hG17 were expressed as a percentage of the total acid output induced by the first injection of hG17.

Figure 2:
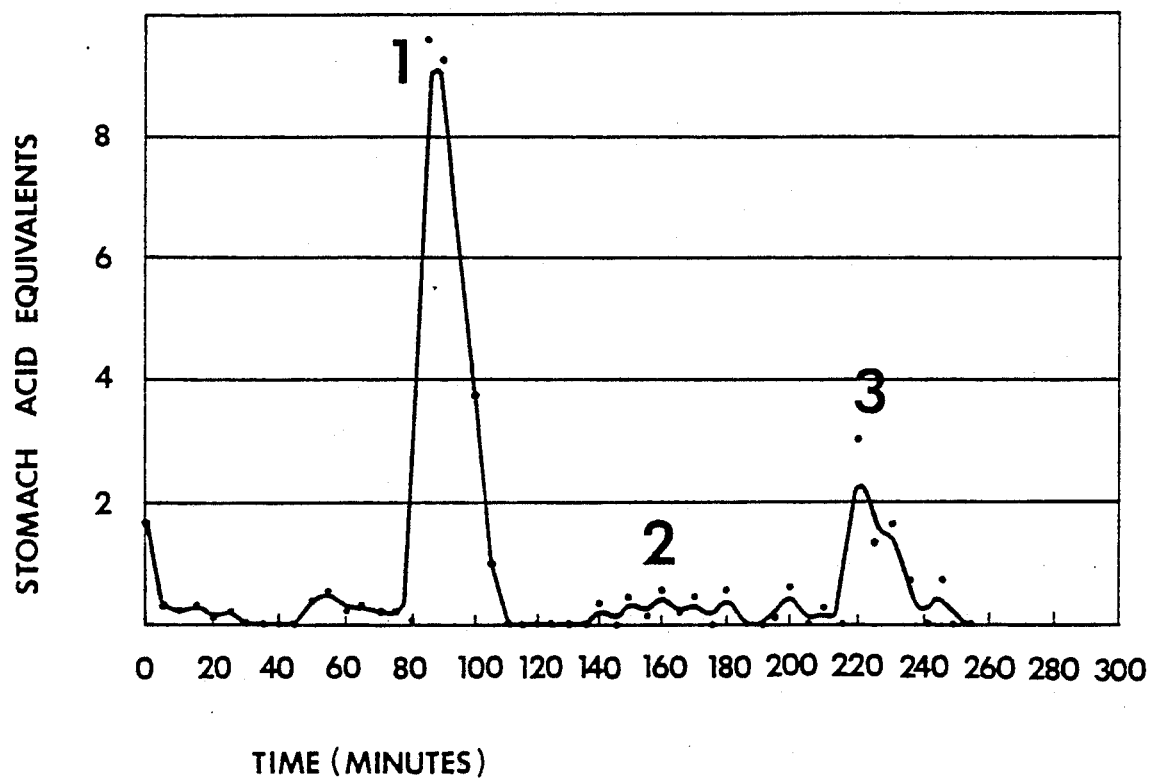
FIG. 2: illustrates the stomach acid secretion over time or a rat injected sequentially with hG17, hG17 premixed with anti hG17 antisera; and hG17.

In five rats tested by this experimental procedure there was an 81%-100% (mean=94%) reduction in the acid secreted by the perfused rat stomach in response to the hormone premixed with anti-hG17 specific antibody (second injection) or to the third injection consisting of free hG17 alone. Control rats experienced little or no reduction in acid secretion stimulated by the second and third injections of hormone. FIG. 1 and FIG. 2 illustrate the responses of a control rat (FIG. 1) and experimental rat (FIG. 2) to these treatments.

EXAMPLE 4

A major application of this invention is the active immunization of humans to induce specific immunity against G17 for ulcer therapy and prevention. In this example, it is demonstrated that active immunization with an anti-G17 immunogen induces antibodies that dramatically suppress G17 mediated release of stomach acid.

To actively immunize rats against G17, we follow the methods used to obtain antisera in the passive immunization tests as described in Example 3. An immunogen consisting of the G17(6) peptide covalently coupled to Diphtheria toxoid (DT) is prepared as described in Example 1. This immunogen is suspended in Phosphate Buffered Saline at a concentration of 4.0 mg/ml. The antigen is emulsified in squalene:arlacel (4:1) vehicle, at a final ratio of 1:1 (antigen:vehicle). Nor-MDP is included in the mixture to give a final concentration of nor-MDP of 200 ug/ml. The final concentration of the DT-G17(6) in the formulation is 2.0 mg/ml. Experimental rats are injected with 0.25 ml of this preparation intraperitoneally. Each injection thus delivers approximately 500 ug of immunogen plus 50 ug of nor-MDP. A second injection is similarly administered 21 days later.

Blood samples for antibody analysis are obtained by tail vein bleeding before the first injection and 14 days after each injection. Sera is prepared by allowing the blood to clot for 30 minutes at room temperature followed by centrifugation at 400×g to remove the clots. The Sera are stored frozen until used.

To determine the antibody responses of the immunized rats, a RIA is employed as described in Example 2. The results of this test show that the immunization procedure induces high titers of antibody against G17. These response are specific for G17; no reactivity is detected with G34, with pentagastrin (the biologically active, carboxy terminal fragment of G17, G34, and CCK), or with CCK. The antibodies are thus directed against the unique epitope on G17 that is selectively targeted by the immunogen. These results are similar to those of Example 2.

The use of the immunogens described herein for the active immunogen is not limited to the adjuvant, vehicle, injection schedule, etc., described above. Any means of safely inducing immunity against G17 using the immunogens described can be applied. This includes using alternative dosages, routes, vehicles, adjuvants, exipients, slow-release compounds, etc.

We test for the neutralization of G17's biological activity in the immunized animals using the perfused rat stomach method, as described in Example 3, with the important difference that we do not inject antisera into the rats (passive immunization) because the actively immunized rats are making their own antibodies against G17. The dosages of compounds administered in these tests, with delivery times of 5 minutes per total dose, are: G17=0.4 ug/kg, G34=0.8 ug/kg, and pentagastrin=2.0 ug/kg. Stomach contents sampling times are 5 minutes per sample. The stomach acid outputs are calculated as the percent of maximal acid output $$= (100)\frac{An - Ab}{A\max - Ab},$$

where An=the acid produced over each 5 minute sampling interval (as determined by titration with NaOH); Amax=the maximal 5 minute release of stomach acid upon stimulation, usually (but not necessarily) by pentagastrin; and Ab=the baseline level of acid present at the time of a given stimulation (with G17, pentagastrin, or G34).

Figure 3:
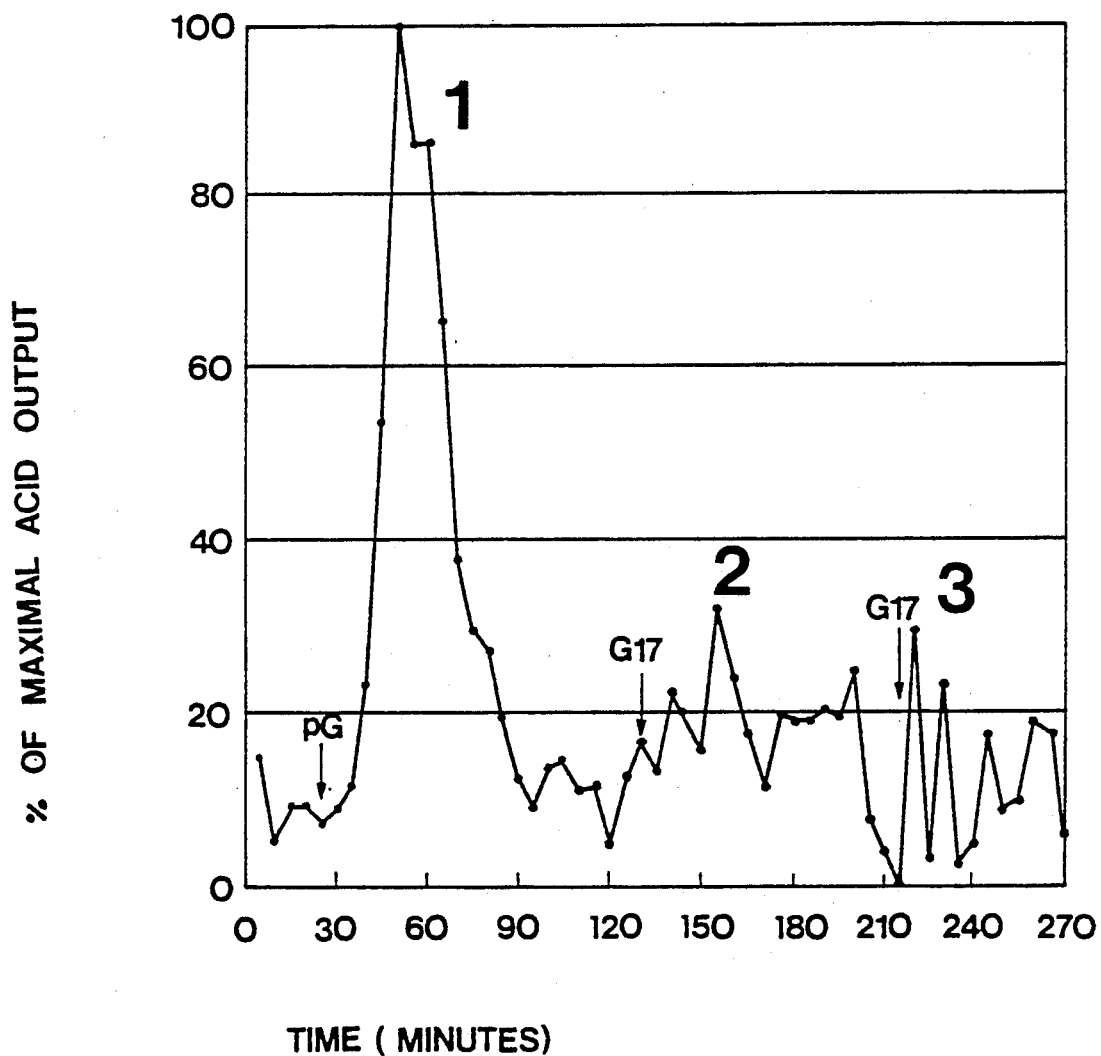
FIG. 3: illustrates the stomach acid output over time in a rat actively immunized against G17 in response to an injection of pentagastrin ("pG") followed by injections of G17.
Figure 4:
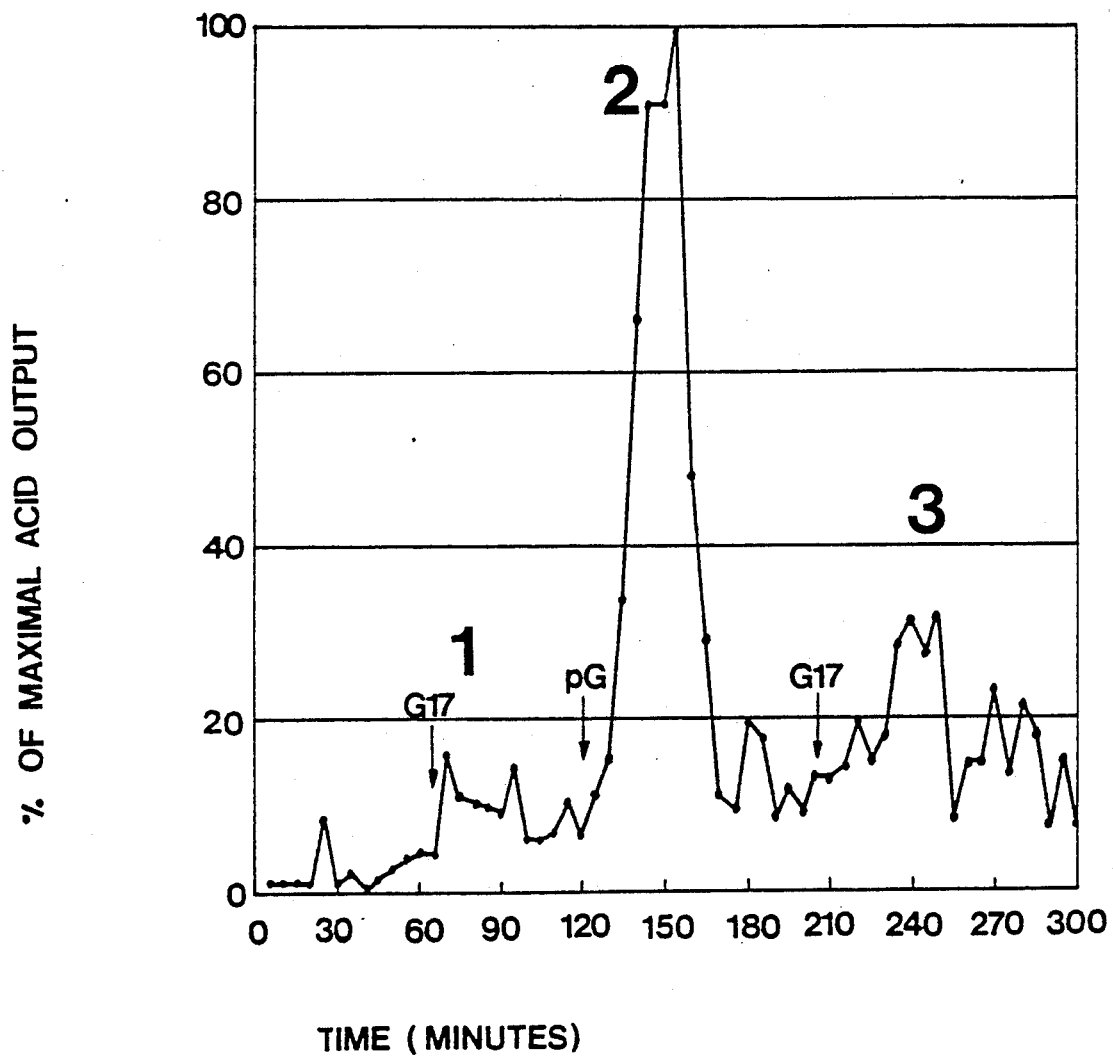
FIG. 4: illustrates the stomach acid output over time in a rat actively immunized against G17 in response to an injection of G17 followed by injections of pentagastrin and G17.

The effects of active immunization against G17 upon the G17 and pentagastrin ("pG") induced acid secretion are shown in FIGS. 3 and 4. The ordinate represents the percent of acid output compared to the maximal acid output induced by pentagastrin. These experiments differed, by design, in the order of G17 and pentagastrin challenge. In both cases, it is clear that in the G17 immunized rats the production of stomach acid in response to G17 (FIG. 3, Peaks 2 and 3; FIG. 4, Peaks 1 and 3) is substantially reduced in comparison with acid secretion induced by pentagastrin (FIG. 3, Peak 1; FIG. 4, Peak 2). The mean reduction in the total G17 mediated acid secretion in our G17 immune rats is 85% (compared to pentagastrin).

Figure 5:
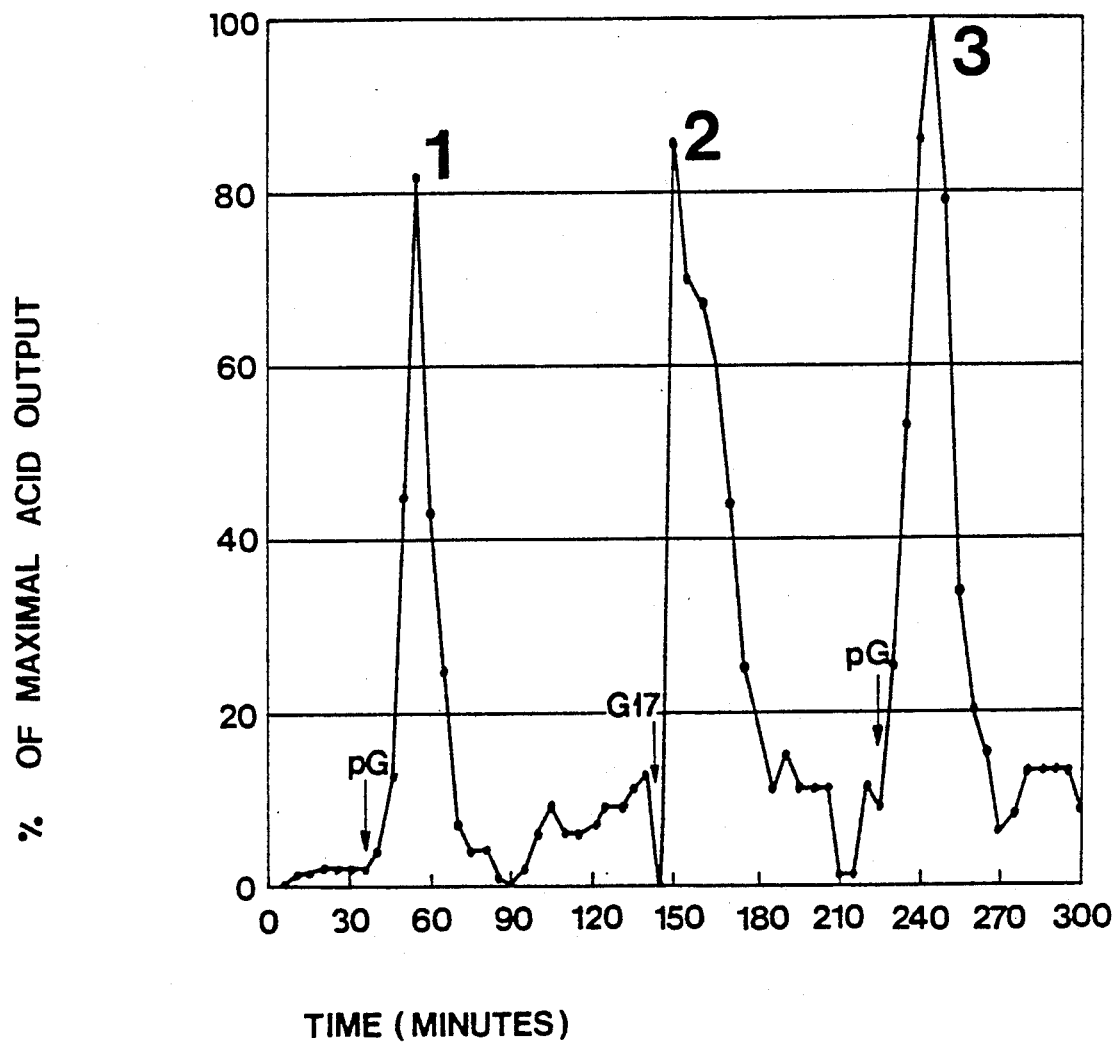
FIG. 5: illustrates the stomach acid output over time in a control rat in response to the sequential injection of pG, G17 and pG.

We verified that the acid reductions were a direct consequence of immunization against G17 by conducting challenges with G17 or pentagastrin in control rats. The control animals were immunized in an identical manner as the G17-immune rats, except that the controls received antigen consisting of DT conjugated to an unrelated peptide (i.e., non-crossreactive with gastrin). RIAs and ELISAs, run on sera from these animals, demonstrated that they produced high antibody titers against both DT and the unrelated peptide, but none against G17, pentagastrin, G34 or CCK. When tested for acid secretion, the control rats responded equally well to challenges with both G17 and pentagastrin. The results of such a test are shown in FIG. 5. This rules out the remote possibility that the neutralization of G17 in the G17-immune rats was caused by non-specific factors (e.g., adjuvant effects, crossreactive anti-DT antibodies, etc.).

A technical challenge presented by the perfused rat stomach assay was the selection of the appropriate acid stimulatory compound for use as a positive control. The exquisite specificity for G17's unique epitope that is characteristic of antibodies induced by our immunogen enabled us to use the ideal control compound: pentagastrin. Pentagastrin comprises the receptor binding/-stimulatory sequence of G17 and also of both G34 and CCK, and it is not bound by antibodies induced by our immunogen. The responses to pentagastrin demonstrated that our immunized animals, acid response mechanism to G17 stimulation were functional. In addition, the pentagastrin responses established the level of acid secretion to be expected from G17 stimulation. The dosages of G17 and pentagastrin, which we determined experimentally, were selected to induce approximately equal acid secretory responses in control rats (see FIG. 5). Thus, we were able to accurately quantitate reductions in acid secretion resulting from the neutralization of G17.

Figure 6:
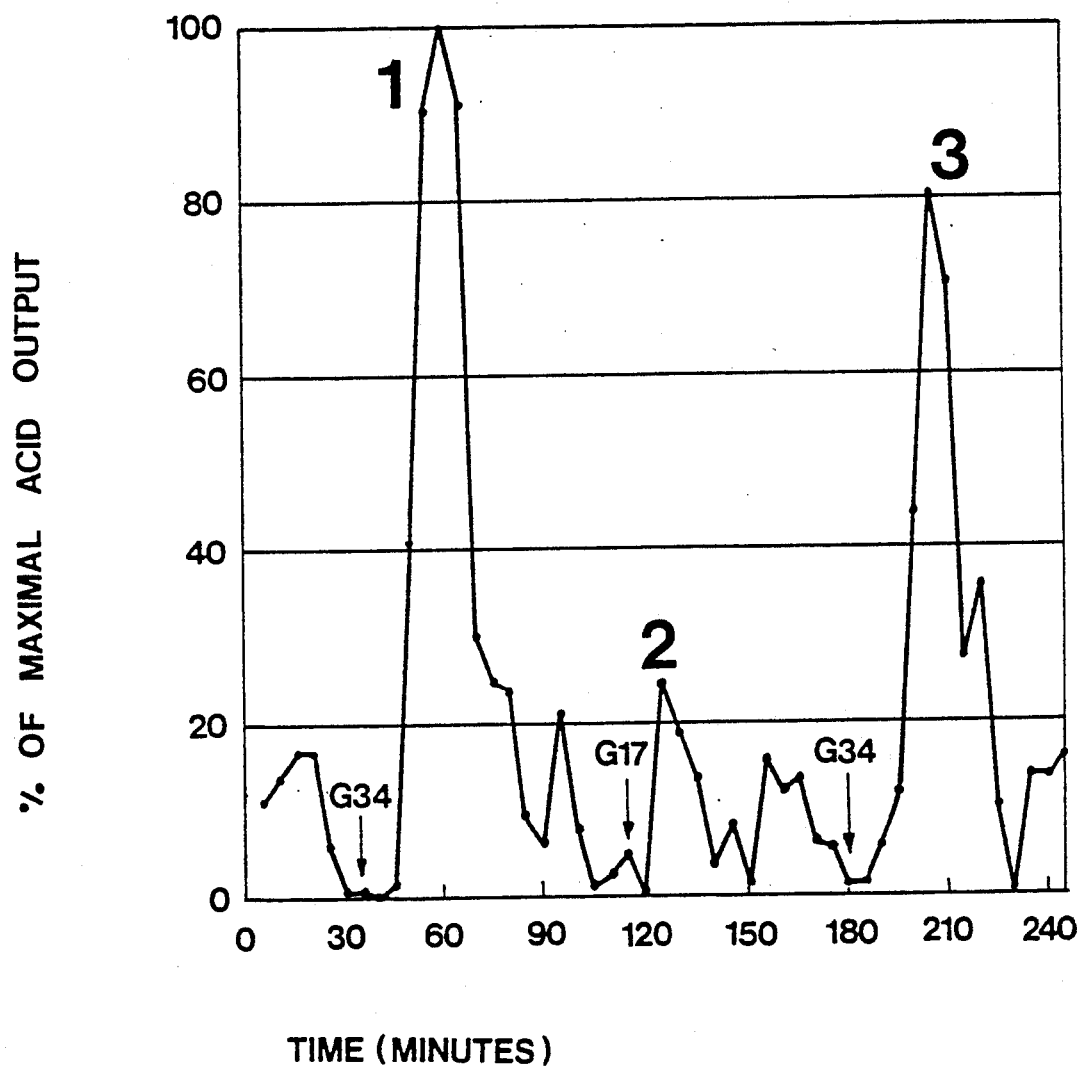
FIG. 6: illustrates stomach acid output over time in a rat actively immunized against G17 in response to sequential injections of G34, G17 and G34.
Figure 7:
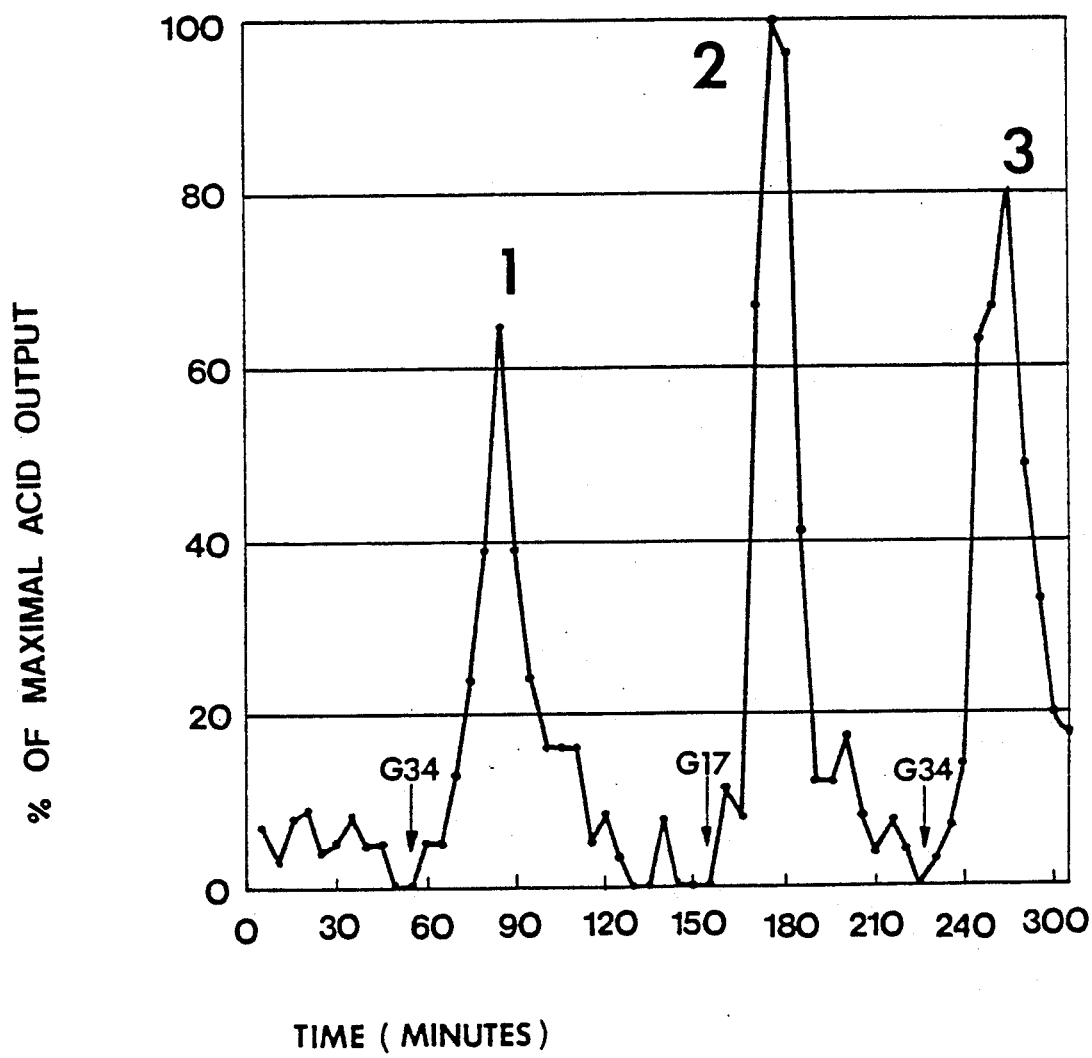
FIG. 7: illustrates stomach acid output over time in a control rat in response to sequential injections of G34, G17 and G34.

For completeness, we have also challenged with G34. We designed our immunogen to specifically neutralize G17 mediated acid secretion (particularly following food intake) and to have no effect upon acid output induced by G34 (which provides for basal stomach activity). Since the antisera from the G17 immune rats do not react with G34, we expected to see no effect upon G34's ability to stimulate acid secretion. Indeed, as shown in FIG. 6, the immunized rats secreted normal quantities of acid in response to G34 stimulation (Peaks 1 and 3). As expected, the injection of G17 failed to induce acid secretion in these animals (FIG. 6, Peak 2). Both G17 and G34 induce strong acid secretory responses in control rats (immunized against an irrelevant peptide), as can be seen in FIG. 7. Clearly, the anti-G17 antibodies induced by our immunogen have no effect upon the functions of other molecules to which the antibodies do not bind. The G17(6) based immunogen described herein induces antibodies that are specific for G17 and neutralize G17's acid releasing activity. Such an immunogen should thus protect against and cure peptic ulcers.

EXAMPLE 5

Synthetic peptides have been produced that contain the unique epitope on G17 and in addition carry reactive groups that can be selectively bound to crosslinking agents. These peptides serve as monomers in the construction of a polymer immunogen. By including two or more reactive groups in each peptide it is possible to construct multi-peptide aggregates, or polymers, by reaction of the groups with a cross-linking agent. Such polymers are then used as immunogens to induce antibodies against the G17 epitope expressed by the peptide. These antibodies bind to G17 in vivo and neutralize G17, thus mediating an anti-ulcer effect. These polymerized peptides have an advantage in that they can be used as immunogens by themselves without a coupling to an immunogenic carrier.

The following peptide designated as Peptide 7 was constructed:

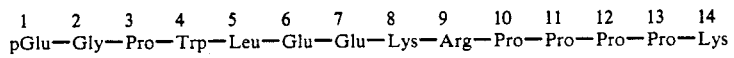

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| pGlu | Gly | Pro | Trp | Leu | Glu | Glu | Lys | Arg | Pro | Pro | Pro | Pro | Lys |

The G17 epitope is contained in amino acids 1-7 of the peptide. Other epitopes e.g. G34 epitopes, can also be used to construct other polymer immunogens according to the invention. Amino acids 8 and 14, which are both Lys, contain amino groups as side groups. These amino groups act as functional groups which are reacted with the functional groups on the crosslinking agent to form the crosslinked peptide polymer. Other amino acids containing side functional groups could be substituted for Lys depending on the reactivity of the functional group with the group on the crosslinking agent to be used. The location of the functional amino acids can be varied in the peptide as long as they are not positioned within the epitope region. Additional reactive amino acids could also be added to increase crosslinking. These additional amino acids could be reactive with the same or alternative crosslinking agents. It follows that more than one type of crosslinking agent can be used.

Amino acids 9-13 comprise a "spacer region" between the reactive amino acids 8 and 14. The composition, number of amino acids and length of the spacer can be varied. If necessary, helper T-cell epitopes can also be included in the peptide.

Peptide 7 was synthesized and purified by standard solid phase peptide synthesis and purification methodologies. Any other method of peptide production well known to those skilled in the art including recombinant DNA technology can also be used to produce the peptides of the invention.

5.0 mg of the peptide was dissolved in 1.0 ml phosphate buffer (0.1 M; pH=6.8). To this was added glutaraldehyde (Grade 1, Sigma Chemical Co.) in a 2:1 molar ratio of glutaraldehyde to peptide. The glutaraldehyde was added dropwise with stirring, at room temperature.

The reaction was allowed to proceed overnight, at room temperature, with stirring. 50.0 mgs. of sodium borohydride were then added slowly to the reaction mixture, and the mixture was stirred at room temperature for an additional hour. The mixture was transferred to dialysis tubing, 1,000 molecular weight cutoff (#132636, Spectrum Medical Industries, Inc.), and exhaustively dialyzed against saline. The peptide-polymer was stored frozen at −20° C.

The polymer was analyzed by SDS-PAGE using a 15% polyacrylamide gel. The electrophoresis demonstrated that the polymerized peptide contained polymers of various sizes comprising multiples of the peptide. The average polymer contained 6 peptides, however; the size of the polymers ranged up to 12 peptides per molecule.

A second polymer was made using the identical procedures, except that a 20:1 molar ratio of glutaraldehyde to peptide was used. The SDS-PAGE analysis of the second polymer similar results with respect to the size range as compared to the 2:1 polymer.

Figure 8:
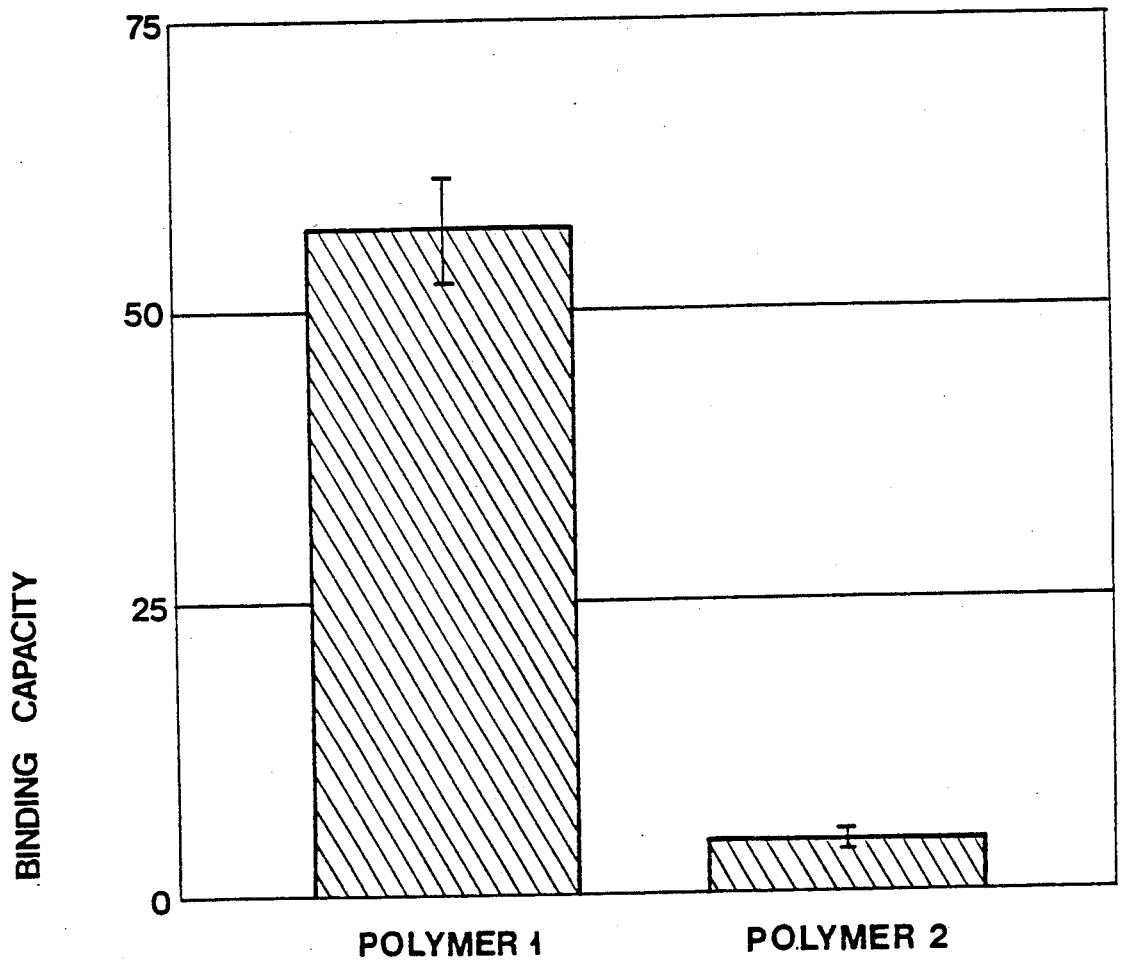
FIG. 8: depicts the binding capacity in picograms ("pg.") of Antigen per microliter ("ul") of sera of anti-G17 antibodies induced by two synthetic peptide antigen epitope polymers of the invention.

Each polymer preparation, 2:1 and 20:1, was used to immunize two separate groups of five mice per group. Prior to injecting the mice with polymer, blood samples were taken from each mouse. The preparation was suspended in Freunds Complete Adjuvant ("FCA") H37Ra (DIFCO Labs) in a 1:1 (vol:vol) ratio of polymer:FCA. The mice were each injected intraperitoneally with 100 ug polymer in 0.2 ml of the mixture. After 21 days each mouse was given a second injection of the same polymer with which it had been injected previously. In the second injection, the antigen was administered intraperitoneally in saline, at 100 ug per mouse. Each mouse was bled 14 days after the second injection and the sera were isolated. The mouse sera were assayed for anti-G17 antibodies by radioimmunoassay (RIA). 1.0 ul of sera was added to 300 ul of buffer (1% BSA in phosphate buffered saline with 0.005M EDTA, pH=7.2). To each of these samples was added 100 ul or 3000 CPM of $^{125}$I-labeled G17 (NEN, Specific activity=12 uCi/ug). The samples were incubated 1.0 hour at room temperature. We next added 100 ul of Calf Serum (Hyclone Labs), immediately followed by 500 ul of 25% polyethylene glycol-8000 (Sigma). The samples were mixed and then centrifuged for 30 minutes at 500×g at room temperature. The supernatant was discarded, and the pellet suspended in 250 ul of saline at 90° C. The suspension was transferred to 3.0 ml of Scintiverse II [Fisher Scientific] in mini vials for liquid scintillation counting. The samples were counted in a Beckman Liquid Scintillation counter (#LS 5000 LE) for $^{125}$I. The binding capacities of the antisera were calculated from the resulting $^{125}$I counts per sample and are depicted in FIG. 8.

Both of the polymers induced anti-G17 antibody responses. Polymer #1, the 2:1 ratio polymer (FIG. 8), induced a very strong response of 56 pg of antigen bound per ul of sera. Polymer #2, the 20:1 ratio polymer (FIG. 8), induced a response that was 10-fold lower. The response induced by polymer #1 is equivalent to that induced by three injections of the G17(6)-DT immunogen of Example 2 in rats.

Thus, polymerized synthetic peptides can be used to induce potent anti-G17 antibody responses.

This invention and its preferred embodiments have been described in detail. It will be appreciated that those skilled in the art, upon consideration of this disclosure, may make modifications and improvements within the scope of this invention.

We claim:

1. An immunogenic composition comprising a peptide selected from the group consisting of pGlu-Gly-Pro-Trp-Leu-Glu-Glu-GLu, pGlu-Gly-Pro-Trp-Leu-Glu-Glu, pGlu-Gly-Pro-Trp-Leu-Glu-, pGlu-Gly-Pro-Trp-Leu, pGlu-Gly-Pro-Trp" to "pGlu-Gly-Pro-Trp-Leu-Glu-Glu-Glu, pGlu-Gly-Pro-Trp-Leu-Glu-Glu, pGlu-Gly-Pro-Trp-Leu-Glu, pGlu-Gly-Pro-Trp-Leu, pGlu-Gly-Pro-Trp", coupled to an immunogenic carrier.

2. A pharmaceutical composition comprising an effective amount of the immunogenic composition of claim 1 in a pharmaceutically acceptable carrier.

3. An immunogenic composition comprising a plurality of peptide monomers wherein each peptide monomer is selected from the group consisting of pGlu-Gly-Pro-Trp-Leu-Glu-Glu-Glu, pGlu-Gly-Pro-Trp-Leu-Glu-Glu, pGlu-Gly-PRo-Trp-Leu-Glu, pGlu-Gly-Pro-Trp-Leu, pGlu-Gly-Pro-Trp said monomers being crosslinked to each other by means of crosslinking agent so as to form a polymer.

4. The immunogenic composition of claim 3 wherein each peptide monomer additionally comprises an amino acid residue containing a side group which is capable of reacting with a crosslinking agent.

5. A pharmaceutical composition comprising an effective amount of the immunogenic composition of claim 3, or 4 in a pharmaceutically acceptable vehicle.

6. The immunogenic composition of claim 1 wherein the immunogenic carrier is diptheria toxoid, tetanus toxoid, keyhole limpet hemocyanin or bovine serum albumin.

7. The immunogenic composition of claim 1 wherein the peptide additionally comprises a spacer peptide sequence.

8. The immunogenic composition of claim 7 wherein the spacer peptide is -Arg-Pro-Pro-Pro-Pro-Cys-.

* * * * *

UNITED STATES PATENT AND TRADEMARK OFFICE
CERTIFICATE OF CORRECTION

PATENT NO. : 5,023,077

DATED : June 11, 1991

INVENTOR(S) : Philip C. Gevas; Stephen L. Karr, Jr.; Stephen Grimes; Richard L. Littenberg It is certified that error appears in the above-identified patent and that said Letters Patent is hereby corrected as shown below:

col. 1, line 59, after "molecule" insert --.--;

col. 1, line 61, after "receptors" insert --.--;

col. 1, line 62, "(C-terminal")" should read --("C-terminal")--;

col. 3, line 24, "b" should read --by--;

col. 5, line 10, "o" should read --of--;

col. 10, line 49, "hCCk" should read --hCCK--;

col. 10, line 51, after ""ABC"" delete --8--;

col. 11, line 4, after "Immunogen" insert --5--;

col. 11, line 45, "an" should read --and--;

col. 13, line 54, "animals," should read --animals'--;

UNITED STATES PATENT AND TRADEMARK OFFICE
CERTIFICATE OF CORRECTION

PATENT NO. : 5,023,077

DATED : June 11, 1991

INVENTOR(S) : Philip C. Gevas; Stephen L. Karr, Jr.; Stephen Grimes; Richard L. Littenberg It is certified that error appears in the above-identified patent and that said Letters Patent is hereby corrected as shown below:

col. 16, lines 23-26, claim 1, after "consisting of" delete
--pGlu-Gly-Pro-Trp-Leu-Glu-Glu-GLu, pGlu-Gly-Pro-Trp-Leu-Glu-Glu, pGlu-Gly-Pro-Trp-Leu-Glu-, pGlu-Gly-Pro-Trp-Leu, pGlu-Gly-Pro-Trp" to "--;

col. 16, line 28, after "pGlu-Gly-Pro-Trp-Leu" insert -- and --;

col. 16, line 29, claim 1, after "pGlu-Gly-Pro-Trp" delete --"--;

col. 16, line 38, claim 3, "pGlu-Gly-PRo-Trp-Leu-Glu" should read --pGlu-Gly-Pro-Trp-Leu-Glu--;

Signed and Sealed this

Second Day of March, 1993

Attest:

STEPHEN G. KUNIN

*Attesting Officer*       *Acting Commissioner of Patents and Trademarks*